US011253721B2

(12) United States Patent
Bae et al.

(10) Patent No.: US 11,253,721 B2
(45) Date of Patent: Feb. 22, 2022

(54) LED LIGHTING APPARATUS HAVING STERILIZING FUNCTION

(71) Applicant: SEOUL VIOSYS CO., LTD., Ansan-si (KR)

(72) Inventors: Hee Ho Bae, Ansan-si (KR); A Young Lee, Ansan-si (KR); Yeong Min Yoon, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 137 days.

(21) Appl. No.: 16/703,067

(22) Filed: Dec. 4, 2019

(65) Prior Publication Data

US 2020/0179712 A1 Jun. 11, 2020

Related U.S. Application Data

(60) Provisional application No. 62/776,566, filed on Dec. 7, 2018.

(51) Int. Cl.
*A61N 5/06* (2006.01)
*F21K 9/65* (2016.01)
(Continued)

(52) U.S. Cl.
CPC .............. *A61N 5/062* (2013.01); *F21K 9/65* (2016.08); *F21V 3/00* (2013.01); *H01L 25/0753* (2013.01);
(Continued)

(58) Field of Classification Search
CPC ........ A61L 2/084; A61L 2/24; A61L 2202/14; A61L 2202/11; A61L 9/20;
(Continued)

(56) References Cited

U.S. PATENT DOCUMENTS 10,309,614 B1 *  6/2019  Jones ........................ F21K 9/61
10,357,582 B1    7/2019  Barron et al.
(Continued)

FOREIGN PATENT DOCUMENTS

KR          10-1075411       10/2011
KR      10-2013-0131584      12/2013
(Continued)

OTHER PUBLICATIONS

International Search Report dated Mar. 20, 2020 on PCT/KR2019/017077.

*Primary Examiner* — Kevin Quarterman
(74) *Attorney, Agent, or Firm* — H.C. Park & Associates, PLC

(57) ABSTRACT

A lighting apparatus including a white light emitting device including at least one first light emitting diode and a wavelength converter, and at least one second light emitting diode emitting light suitable for producing a cell activating substance, in which the first light emitting diode emits light having a central wavelength in a range of about 300 nm to about 420 nm, the second light emitting diode emits light having a central wavelength in a range of about 605 nm to about 935 nm, the wavelength converter includes wavelength conversion substances to convert light of the first light emitting diode into white light, and, in irradiance spectrum of the white light implemented in the white light emitting device, an irradiance at the central wavelength of light emitted from the first light emitting diode is less than that at a peak wavelength of blue light emitted from the wavelength conversion substance.

23 Claims, 7 Drawing Sheets

(51) Int. Cl.
*F21V 3/00* (2015.01)
*H01L 33/50* (2010.01)
*H01L 25/075* (2006.01)
*H01L 33/62* (2010.01)
*F21Y 115/10* (2016.01)
*F21Y 113/13* (2016.01)

(52) U.S. Cl.
CPC .......... *H01L 33/504* (2013.01); *H01L 33/505* (2013.01); *H01L 33/507* (2013.01); *H01L 33/62* (2013.01); *A61N 2005/066* (2013.01); *A61N 2005/0661* (2013.01); *A61N 2005/0663* (2013.01); *F21Y 2113/13* (2016.08); *F21Y 2115/10* (2016.08)

(58) Field of Classification Search
CPC ... H01L 25/0753; H01L 33/62; H01L 33/507; H01L 33/505; H01L 33/504; H01L 33/502; F21K 9/62; F21Y 2115/10; F21Y 2113/13; H05B 45/10; H05B 45/20
See application file for complete search history.

(56) References Cited

U.S. PATENT DOCUMENTS

| | | | |
|---|---|---|---|
| 10,617,774 B2 * | 4/2020 | Winslow | F21V 15/015 |
| 2016/0030610 A1 * | 2/2016 | Peterson | A61L 2/084 |
| | | | 362/84 |
| 2016/0375161 A1 * | 12/2016 | Hawkins | F21V 23/0442 |
| | | | 422/22 |

FOREIGN PATENT DOCUMENTS

| | | |
|---|---|---|
| KR | 10-1769392 | 8/2017 |
| KR | 10-2018-0036728 | 4/2018 |
| KR | 10-1848254 | 4/2018 |

* cited by examiner

LED LIGHTING APPARATUS HAVING STERILIZING FUNCTION

CROSS-REFERENCE TO RELATED APPLICATIONS

This application claims priority to and the benefit of U.S. Provisional Application No. 62/776,566, filed on Dec. 7, 2018, which is hereby incorporated in its entirety by reference for all purposes as set forth herein.

BACKGROUND

Technical Field

Exemplary embodiments of the invention relate to a lighting apparatus having a cell activating function.

As an inorganic light source, light emitting diodes have been used in various fields including displays, vehicular lamps, general lighting, and the like. In particular, with various advantages, such as long lifespan, low power consumption, and rapid response, light emitting diodes have been replacing conventional light sources.

Sunlight exhibits a broad spectrum of wavelengths in the ultraviolet, visible, and infrared regions. The human body has survived by adapting to sunlight, and in particular, cells in the human body absorb light of wavelengths near the near infrared to use for cell activity.

Meanwhile, it is well known in the art that ultraviolet rays are generally harmful to the human body, particularly to the eyes or skin. In addition, some wavelength bands in the blue wavelength region may cause eye diseases or skin diseases.

The above information disclosed in this Background section is only for understanding of the background of the inventive concepts, and, therefore, it may contain information that does not constitute prior art.

SUMMARY

Exemplary embodiments provide a lighting apparatus having a cell activating function without causing eye diseases, skin diseases, and the like, and a lighting system having the same.

Exemplary embodiments also provide a lighting apparatus capable of changing color temperature over time like sunlight, and having a cell activating function and a lighting system having the same.

Exemplary embodiments further provide a lighting apparatus capable of changing color temperature in consideration of the color temperature of sunlight according to a region and time, and having a cell activating function, and a lighting system having the same.

Additional features of the inventive concepts will be set forth in the description which follows, and in part will be apparent from the description, or may be learned by practice of the inventive concepts.

A lighting apparatus according to an exemplary embodiment includes: a white light emitting device including at least one first light emitting diode and a wavelength converter to implement white light; and at least one second light emitting diode emitting light suitable for producing a cell activating substance, in which the first light emitting diode emits light having a central wavelength in a range of about 300 nm to about 420 nm, the second light emitting diode emits light having a central wavelength in a range of about 605 nm to about 935 nm, the wavelength converter includes a plurality of wavelength conversion substances to convert light of the first light emitting diode into white light, the lighting apparatus emits the white light implemented in the white light emitting device and light generated by the second light emitting diode to the outside, and, in irradiance spectrum of the white light implemented in the white light emitting device, an irradiance at the central wavelength of light emitted from the first light emitting diode is less than that at a peak wavelength of blue light emitted from the wavelength conversion substance.

The lighting apparatus having a cell activating function may be provided by using the second light emitting diode suitable for producing a cell activating substance together with the white light emitting device. Since an irradiance of light emitted from the first light emitting diode is less than that of the peak wavelength of blue light emitted from the wavelength conversion substance, the lighting apparatus may prevent the first light emitting diode from causing harm to the human body or from causing eye diseases or skin diseases.

The cell activating substance may be nitric oxide (NO) produced by cytochrome c oxidase activity in mitochondria. NO improves the health of the human body by affecting pain relief and improving blood circulation.

Light of the second light emitting diode absorbed by the intracellular mitochondria may cause the mitochondria to produce more ATPs and enhance metabolism.

The second light emitting diode may emit light having a central wavelength of about 605 nm to about 655 nm, about 685 nm to about 705 nm, about 790 nm to about 840 nm, or about 875 nm to about 935 nm. In these wavelength ranges, an energy absorption rate of cytochrome c oxidase is relatively higher. In particular, the cytochrome c oxidase exhibits the highest absorption in the range of 790 nm to 840 nm, and followed by in the range of 875 nm to 935 nm. Accordingly, the second light emitting diode may include a light emitting diode having a central wavelength at least in the range of 790 nm to 840 nm or in the range of 875 nm to 935 nm.

The wavelength converter may include wavelength conversion substances for converting light of the first light emitting diode into blue, green, and red light.

The wavelength converter may include blue and orange wavelength conversion substances for converting light of the first light emitting diode into blue and orange light.

The white light and light emitted from the second light emitting diode may be mixed and emitted. The lighting apparatus may further include a diffusion plate for mixing the white light and light emitted from the second light emitting diode.

The wavelength converter may include a phosphor or a quantum dot. The wavelength converter may include a blue phosphor, a green phosphor, and a red phosphor, each of which may be replaced with quantum dots.

Light emitted from the second light emitting diode may be emitted to the outside without passing through the wavelength converter.

A portion of light emitted from the second light emitting diode may be wavelength-converted by the wavelength converter.

The first light emitting diode may emit light having a central wavelength in a range of about 400 nm to about 420 nm, such that a light conversion efficiency as compared to ultraviolet rays.

An irradiance of light generated by the at least one second light emitting diode and emitted to the outside may be greater than that of red light wavelength-converted by the wavelength converter and emitted. Accordingly, the cell activating substance may be produced using the second light emitting diode.

The lighting apparatus may include a greater number of first light emitting diodes than that of the at least one second light emitting diode. Accordingly, the irradiance of the white light emitting device may be greater than that of the second light emitting diode.

An irradiance of light generated by the at least one second light emitting diode and emitted to the outside may be less than or equal to 570 W/m².

The lighting apparatus may further include a circuit board for mounting the first light emitting diode and the second light emitting diode.

The lighting apparatus may include a location information receiver for receiving location information; and a controller for receiving the location information from the location information receiver and controlling a dose of light emitted from the white light emitting device; in which the controller may calculate a dose of light to be emitted by the white light emitting device based on the location information, and may control the white light emitting device to emit light in an amount equivalent to the dose.

The controller may calculate an appropriate dose based on the location information provided by the location information receiver, and may control the light source to emit the appropriate dose.

The location information receiver may calculate location information of the lighting apparatus, the controller may receive the location information and calculate a dose of external light and an appropriate dose at the place where the lighting apparatus is located, and may control the white light emitting device to emit light in an amount equivalent to a difference between the appropriate dose and the dose of external light.

The controller may calculate time information from the location information and may control a dose of light to be emitted by the white light emitting device according to the time information.

A lighting apparatus according to another exemplary embodiment includes: a first light emitting unit including a first first-light emitting diode emitting light having a central wavelength in a range of about 300 nm to about 420 nm and a first wavelength converter; a second light emitting unit including a first second-light emitting diode emitting light having a central wavelength in a range of about 300 nm to about 470 nm and a second wavelength converter; at least one second light emitting diode emitting light having a central wavelength in a range of about 605 nm to about 935 nm, in which the first light emitting unit emits light of a higher color temperature than that of the second light emitting unit, the first wavelength converter includes a blue wavelength conversion substance for converting light emitted from the first first-light emitting diode into blue light, and, in irradiance spectrum of light emitted to the outside, an irradiance at the central wavelength of light generated by each light emitting diode in the first and second light emitting units and emitted to the outside without wavelength conversion is less than that at a peak wavelength of wavelength-converted light emitted from the first and second wavelength converters.

Since a plurality of light emitting units are included, a lighting apparatus may implement white light having various color temperatures. Accordingly, the lighting apparatus may change the color temperature to suit the change of sunlight over time. In addition, intensity of blue light emitted from the light emitting diodes of the lighting apparatus to the outside may be less than that of light wavelength-converted by the wavelength converter, and thus, the occurrence of eye diseases and skin diseases caused by the light emitting diode may be prevented.

The lighting apparatus may further include a third light emitting unit including a first third-light emitting diode emitting light having a central wavelength in a range of about 300 nm to about 470 nm and a third wavelength converter, in which the third light emitting unit emits light of a higher color temperature than that of the second light emitting unit, and, in irradiance spectrum of light emitted to the outside, an irradiance at the central wavelength of light generated by the first third-light emitting diode in the third light emitting unit and emitted to the outside without wavelength conversion is less than that at a peak wavelength of wavelength-converted light emitted from the third wavelength converter.

The first to third wavelength converters may further include a green wavelength conversion substance for converting light emitted from the first light emitting diode into green light, and a red wavelength conversion substance for converting light emitted from the first light emitting diode into red light, respectively. Accordingly, the first to third light emitting units may implement white light, respectively.

The first light emitting unit, the second light emitting unit, and the third light emitting unit may be driven independently from one another.

The first first- to first third-light emitting diodes may emit light having a central wavelength in a range of about 400 nm to about 420 nm. The first first- to first third-light emitting diodes may emit light having the same peak wavelength.

The cell activating substance may be nitric oxide (NO) produced by cytochrome c oxidase activity in mitochondria. Further, light of the second light emitting diode absorbed by the intracellular mitochondria causes the mitochondria to produce more ATPs and enhance metabolism.

The second light emitting diode may emit light having a central wavelength of about 605 nm to about 655 nm, about 685 nm to about 705 nm, about 790 nm to about 840 nm, or about 875 nm to about 935 nm. In these wavelength ranges, an energy absorption rate of the cytochrome c oxidase is relatively higher.

Light wavelength-converted by the wavelength converter and light emitted from the second light emitting diode may be mixed and emitted to the outside. The mixed light may be white light.

The lighting apparatus may further include a diffusion plate to mix light wavelength-converted by the wavelength converter and light emitted from the second light emitting diode.

The first first- to first third-light emitting diodes may be disposed more than the at least one second light emitting diode, respectively.

The lighting apparatus may further include a circuit board on which the first first- to first third-light emitting diodes and the second light emitting diode are mounted.

The lighting apparatus may further include a location information receiver for receiving location information, and a controller for controlling a dose of light emitted from the first to third light emitting units, in which the controller may control the dose of light emitted from the first to third light emitting units based on the location information.

The controller may calculate an appropriate dose based on the location information provided by the location information receiver, and may control the first to third light emitting units to emit the appropriate dose.

The location information receiver may calculate location information of the lighting apparatus, the controller may receive the location information and calculate a dose of external light and an appropriate dose at the place where the lighting apparatus is located, and may control the first to third light emitting units to emit light in an amount equivalent to a difference between the appropriate dose and the dose of external light.

The controller may calculate time information from the location information and may control a dose of the light according to the time information.

A lighting system according to exemplary embodiments may include a lighting apparatus installed indoors, in which the lighting apparatus is one of the lighting apparatuses described above.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION

Figure 1:
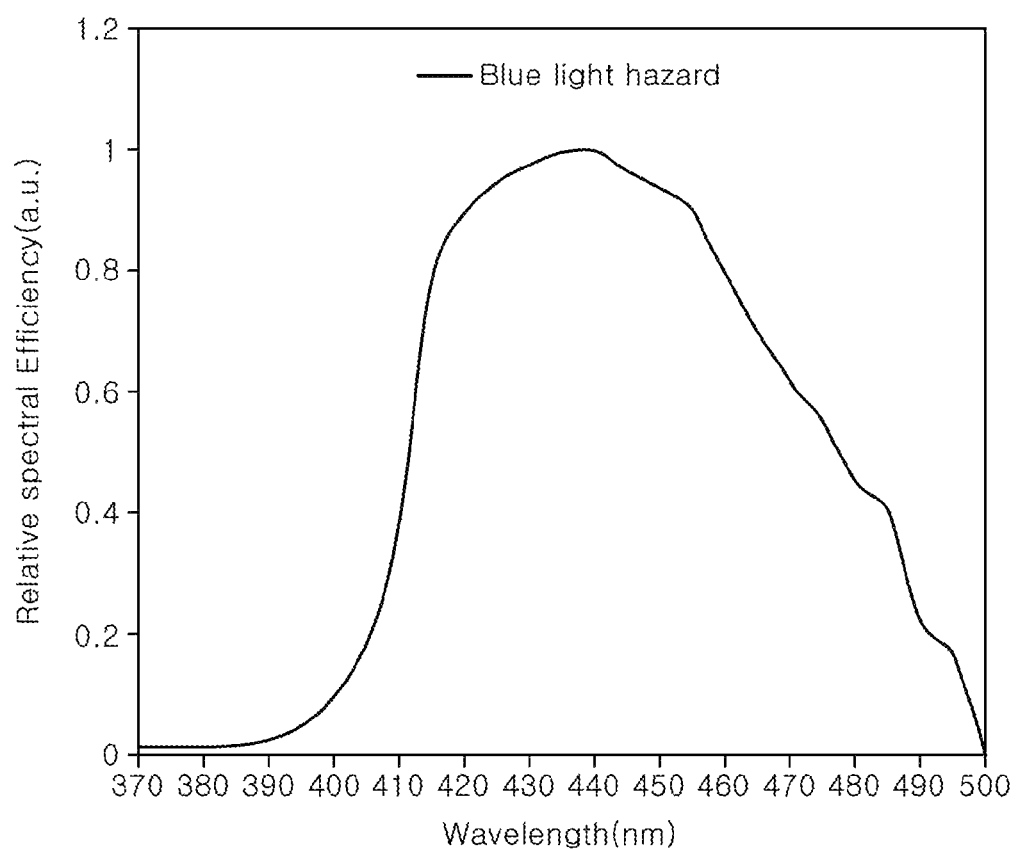
FIG. 1 is a graph showing a degree of hazard according to wavelengths of blue light.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, exemplary embodiments will be described in detail with reference to the accompanying drawings.

FIG. 1 is a graph showing a degree of hazard according to wavelengths of blue light.

Blue light is known to cause eye diseases and skin diseases. In particular, blue light exhibits the highest degree of hazard between 430 nm and 440 nm. A wavelength range of 420 nm to 455 nm exhibits 90% or more degree of hazard based on the highest hazard value, and a wavelength range of 413 nm to 465 nm exhibits 70% or more degree of hazard, and a wavelength range of 411 nm to 476 nm exhibits 50% or more degree of hazard.

It is well known in the art that ultraviolet rays harm the human body and exhibit the highest degree of hazard, especially between 270 nm and 280 nm.

Figure 2:
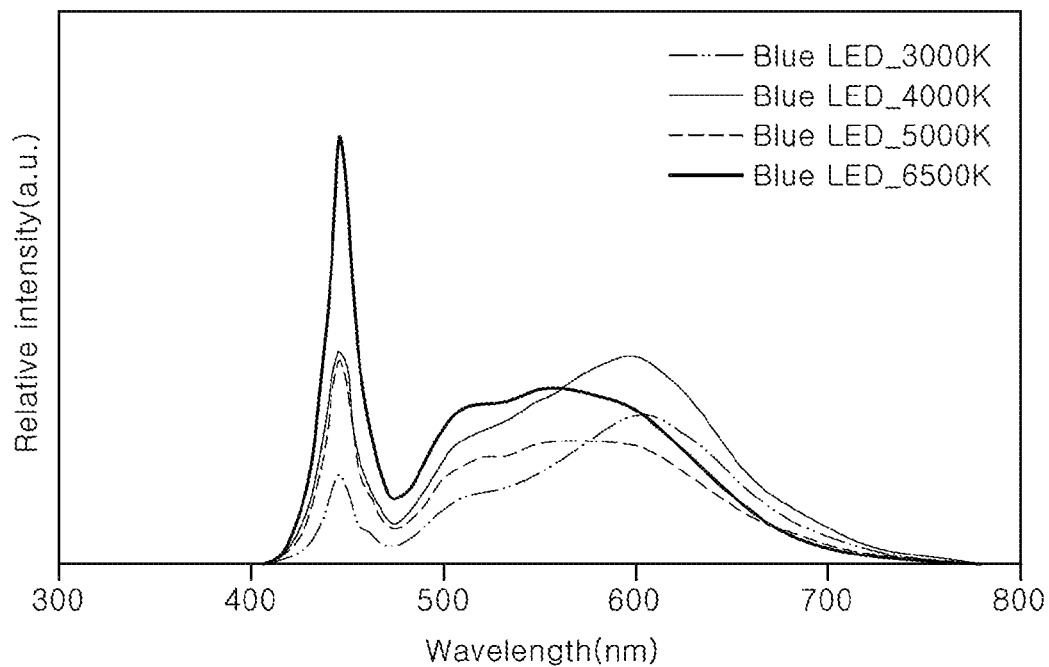
FIG. 2 shows a spectrum of a white light source using a conventional blue light emitting diode.

FIG. 2 shows a spectrum of a white light source using a conventional blue light emitting diode.

Referring to FIG. 2, the conventional white light source implements white light using a yellow phosphor, or a green phosphor and a red phosphor together with a blue light emitting diode. The type of phosphor and the amount of phosphor are controlled according to a color temperature, and an intensity of the blue light generally increases as the color temperature increases.

A blue light emitting diode used in the conventional white light source generally has a central wavelength (e.g., peak wavelength) in a range of 430 nm to 470 nm. Blue light in this range has a relatively high degree of hazard as shown in FIG. 1. As such, as the color temperature of the white light source increases, the intensity of the blue light may be increased thereby increasing the hazard of causing eye diseases or skin diseases.

Figure 3:
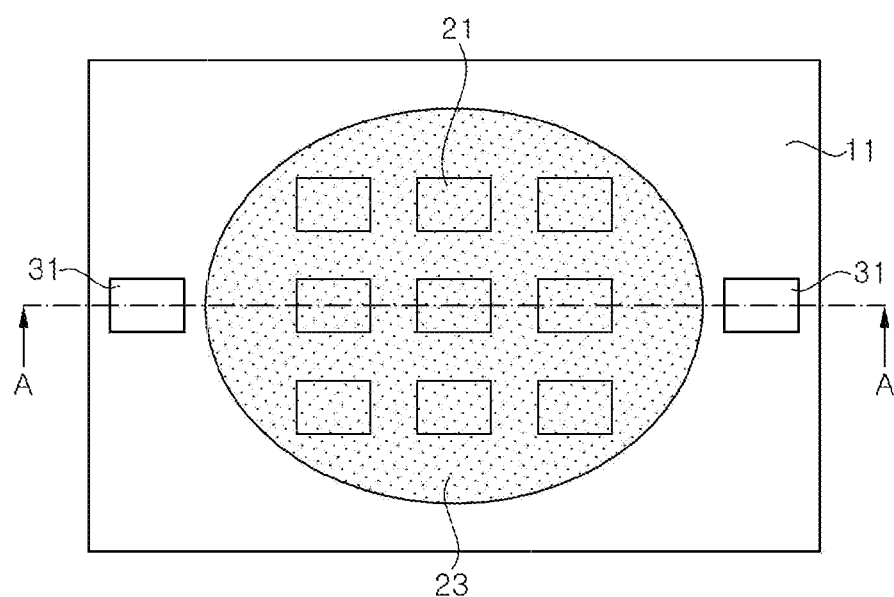
FIG. 3 is a schematic plan view illustrating a lighting apparatus according to an exemplary embodiment.
Figure 4:
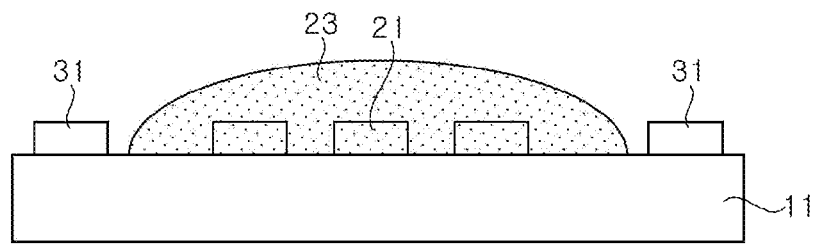
FIG. 4 is a schematic cross-sectional view taken along line A-A of FIG. 3.

FIG. 3 is a schematic plan view illustrating a lighting apparatus according to an exemplary embodiment, and FIG. 4 is a schematic cross-sectional view taken along line A-A of FIG. 3.

Referring to FIG. 3 and FIG. 4, the lighting apparatus may include a circuit board 11, a first light emitting diode 21, a wavelength converter 23, and a second light emitting diode 31.

The circuit board 11 may have a circuit pattern for supplying power to the first and second light emitting diodes 21 and 31. The circuit board 11 may be a printed circuit board, for example, a metal-PCB.

At least one first light emitting diode 21 is mounted on the circuit board 11 as a light source for implementing white light. A plurality of first light emitting diodes 21 may be electrically connected to one another in various ways, for example, may be connected in series, in parallel, or in series parallel.

The first light emitting diode 21 may have, for example, a central wavelength in a range of about 300 nm to 420 nm, and may further have a central wavelength in a range of 400 nm to 420 nm. In this manner, a substantial portion of light emitted from the first light emitting diode 21 may be wavelength-converted by the wavelength converter 23. When the first light emitting diode 21 emits ultraviolet rays, most of ultraviolet rays are wavelength-converted by the wavelength converter 23, thereby preventing ultraviolet rays from being emitted to the outside. Furthermore, when the first light emitting diode 21 has the central wavelength in the range of 400 nm to 420 nm, safety problems caused by ultraviolet rays may be eliminated in advance.

The wavelength converter 23 converts a wavelength of light emitted from the first light emitting diode 21. The wavelength converter 23 may be, for example, a molding member including a phosphor or a quantum dot. The wavelength converter 23 covers the first light emitting diode 21. When the plurality of first light emitting diodes 21 are mounted on the circuit board 11, the wavelength converter 23 may cover each of the plurality of first light emitting diodes 21.

The wavelength converter 23 includes a wavelength conversion substance for implementing white light together with light of the first light emitting diode 21. For example, the wavelength converter 23 may include a blue phosphor, a green phosphor, and a red phosphor. As another example, the wavelength converter 23 may include a blue phosphor and an orange phosphor, or a quantum dot.

The blue phosphor may include a BAM-based, a halophosphate-based, or an aluminate-based phosphor, and may include, for example, $BaMgAl_{10}O_{17}:Mn^{2+}$, $BaMgAl_{12}O_{19}:Mn^{2+}$ or $(Sr,Ca,Ba)PO_4Cl:Eu^{2+}$. The blue phosphor may have, for example, a peak wavelength in a range of 440 nm to 500 nm.

The green phosphor may include $LuAG(Lu_3(Al,Gd)_5O_{12}:Ce^{3+})$, $YAG(Y_3(Al,Gd)_5O_{12}:Ce^{3+})$, $Ga-LuAG((Lu,Ga)_3(Al,Gd)_5O_{12}:Ce^{3+})$, $Ga-YAG$ $((Ga,Y)_3(Al,Gd)_5O_{12}:Ce^{3+})$, $LuYAG((Lu,Y)_3(Al,Gd)_5O_{12}:Ce^{3+})$, ortho-silicate $((Sr,Ba,Ca,Mg)_2SiO_4:Eu^{2+})$, oxynitride $((Ba, Sr,Ca)Si_2O_2N_2:Eu^{2+})$, or thio gallate $(SrGa_2S_4:Eu^{2+})$. The green phosphor may have a peak wavelength in a range of 500 nm to 600 nm.

The red phosphor may include a nitride-based, a sulfide-based, a fluoride or an oxynitride-based phosphor, and, specifically, may include $CASN(CaAlSiN_3:Eu^{2+})$, $(Ba,Sr,Ca)_2Si_5N_8:Eu^{2+}$, $(Ca,Sr)S_2:Eu^{2+})$, or $(Sr,Ca)_2SiS_4:Eu^{2+}$. The red phosphor may have a peak wavelength in a range of 600 nm to 700 nm.

Figure 5:
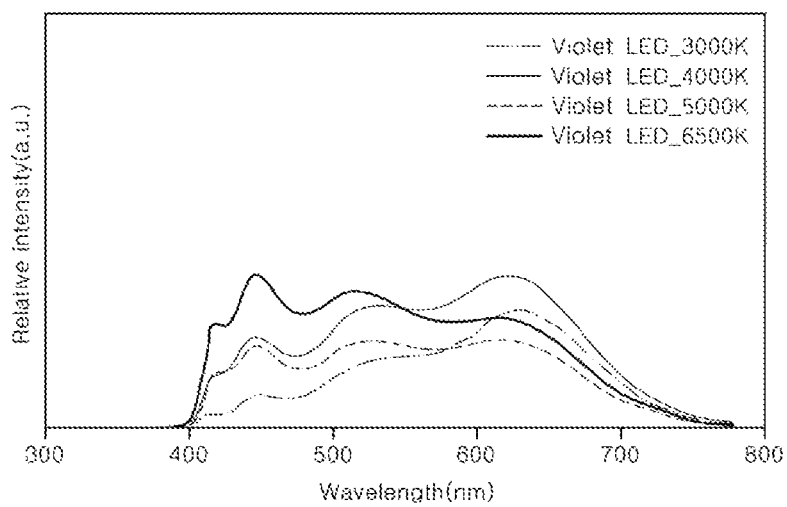
FIG. 5 shows representative spectra of a lighting apparatus according to an exemplary embodiment.

White light may be implemented by a combination of the first light emitting diode 21 and the wavelength converter 23. FIG. 5 shows spectra of white light having various color temperatures implemented by the combination of the first light emitting diode 21 and the wavelength converter 23.

As shown in FIG. 5, white light of each color temperature is implemented by the combination of light emitted from the first light emitting diode 21 and light emitted from the phosphors. In addition, it can be confirmed that irradiance of light emitted from the first light emitting diode 21 at all color temperatures is smaller than that of light emitted from the blue phosphor. As the color temperature increases, although the irradiance of light emitted from the first light emitting diode 21 increases, the irradiance of blue light emitted from the blue phosphor increases at a greater extent. In addition, the irradiance of light emitted from the first light emitting diode 21 may be less than that of light emitted from the green phosphor, and may be less than that of light emitted from the red phosphor.

Accordingly, the lighting apparatus may prevent eye diseases or skin diseases from being caused by light emitted from the first light emitting diode 21.

Referring back to FIG. 3 and FIG. 4, the second light emitting diode 31 may be spaced apart from the wavelength converter 23 to be mounted on the circuit board 11. Light emitted from the second light emitting diode 31 may be emitted to the outside without actually entering the wavelength converter 23. Accordingly, irradiance of light emitted from the second light emitting diode 31 may be improved.

The second light emitting diode 31 may be connected to the first light emitting diode 21 in series or in parallel, and may be driven independently from the first light emitting diode 21.

The second light emitting diode 31 emits light suitable for cell activation. The second light emitting diode 31 may emit light having a central wavelength in a range of, for example, about 605 nm to about 935 nm.

Red light or near infrared light in the range of about 605 nm to about 935 nm produces a cell activating substance in the mitochondria. More particularly, the cytochrome c oxidase in the mitochondria absorbs light in the range of about 605 nm to about 935 nm as a photoreceptor to increase its activity, thereby producing nitric oxide NO. NO improves human health by affecting pain relief and improving blood circulation. In addition, the activity of the cytochrome c oxidase protein contributes to ATP production, and also affects cell damage treatment.

In particular, the second light emitting diode 31 may emit light having a central wavelength in a range of about 605 nm to about 655 nm, about 685 nm to about 705 nm, about 790 nm to about 840 nm, or about 875 nm to about 935 nm. In these wavelength ranges, an energy absorption rate of cytochrome c oxidase is relatively higher. In particular, the cytochrome c oxidase exhibits the highest absorption in the range of 790 nm to 840 nm, followed by in the range of 875 nm to 935 nm, and then in the range of 605 nm to 655 nm.

Since the second light emitting diode 31 emits light having a wavelength in which the energy absorption of the cytochrome c oxidase is high, the efficiency of health promotion may be improved.

Furthermore, when a plurality of second light emitting diodes 31 are used, it is possible to use the plurality of light emitting diodes emitting light in a specific wavelength range among the above wavelength ranges, for example, in the high efficiency range of 790 nm to 840 nm, or 875 nm to 935 nm, and various light emitting diodes may be used to evenly emit light in each of the wavelength ranges.

In addition, since the light emitting diode emitting light in the range of 605 nm to 655 nm may affect the color temperature of the white light, light emitting diodes emitting light having a central wavelength in a low visibility range, that is, in the range of about 685 nm to about 705 nm, about 790 nm to about 840 nm, or about 875 nm to about 935 nm may be mainly used, so as not to affect the color temperature of the white light emitting device.

To add the cell activating function to the lighting apparatus according to an exemplary embodiment, the irradiance of light emitted from the second light emitting diode 31 is greater than that of light emitted from the white light emitting device at the same wavelength. Furthermore, the irradiance of light emitted from the second light emitting diode 31 may be greater than that of light emitted to the outside of the lighting apparatus from the first light emitting diode 21 having the central wavelength in the range of 300 nm to 420 nm. Accordingly, the lighting apparatus according to the illustrated exemplary embodiment has the major cell activating function provided by the second light emitting diode 31, compared to the first light emitting diode 21.

A driving time of the second light emitting diode 31 and that of the first light emitting diode 21 may be substantially the same, however, the inventive concepts are not limited thereto. For example, in some exemplary embodiments, the driving time of the second light emitting diode 31 may be adjusted according to an installation location of the lighting apparatus. In particular, a period of use of the second light emitting diode 31 or the magnitude of the irradiance thereof may be adjusted in consideration of the hazard to the human body.

For example, the irradiance of the second light emitting diode 31 emitted from the lighting apparatus may be 570 W/m2 or less, and further, may be 100 W/m2 or less. 570 W/m2 represents a limit value of risk group 1 for light in the infrared range in the Photobiological Safety Standard (IEC 62471), and 100 W/m2 corresponds to an exempt. The lighting apparatus has the radiance of 570 W/m2 or less, and thus, the lighting apparatus may be driven to produce a cell activating substance without harming the human body for a relatively long period of time.

In an exemplary embodiment, the number of the first light emitting diodes 21 in the lighting apparatus may be greater than the number of the second light emitting diode 31, and thus, the lighting apparatus may emit light having an intensity suitable for illumination. However, the inventive concepts are not limited thereto.

According to an exemplary embodiment, the lighting apparatus may be used to promote the health of the human body not only in the indoor living space but also in a space where a large number of people are active, such as an airport or a hospital.

Figure 6:
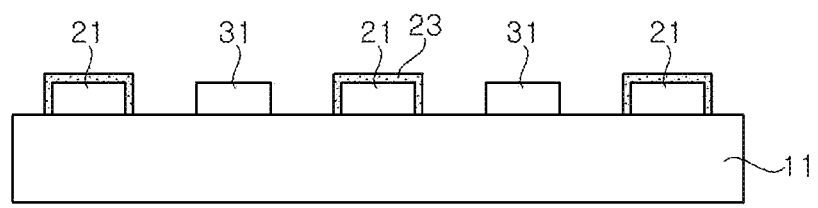
FIG. 6 is a schematic cross-sectional view illustrating a lighting apparatus according to another exemplary embodiment.

FIG. 6 is a schematic cross-sectional view illustrating a lighting apparatus according to another exemplary embodiment.

Referring to FIG. 6, the lighting apparatus according to the illustrated exemplary embodiment is generally similar to the lighting apparatus described with reference to FIG. 3 and FIG. 4, except that wavelength converters 23 are formed on the first light emitting diodes 21, respectively. More particularly, the wavelength converter 23 in FIG. 3 and FIG. 4 covers each of the plurality of first light emitting diodes 21, however, according to the illustrated exemplary embodiment, each of the first light emitting diodes 21 is individually covered with the wavelength converter 23.

The wavelength conversion substances in the first light emitting diode 21 and the wavelength converter 23 are the same as those described above, and thus, repeated descriptions thereof will be omitted.

Since the first light emitting diodes 21 according to the illustrated exemplary embodiment are respectively covered with the wavelength converters 23, the second light emitting diode 31 may be disposed between the first light emitting diodes 21. In particular, as shown in the drawing, the second light emitting diodes 31 may be uniformly disposed between the first light emitting diodes 21, and thus, light emitted from the second light emitting diode 31 may be mixed with the white light. As such, the lighting apparatus according to the illustrated exemplary embodiment is capable of mitigating the external recognition of light emitted from the second light emitting diode 31. In some exemplary embodiments, the second light emitting diodes 31 may be covered with a transparent molding member to protect it from the external environment.

The second light emitting diodes 31 may be connected in series or in parallel to the first light emitting diodes 21, but the inventive concepts are not limited thereto. For example, in some exemplary embodiments, the second light emitting diodes 31 may be mounted on the circuit board 11 to be driven independently from the first light emitting diodes 21.

Figure 7:
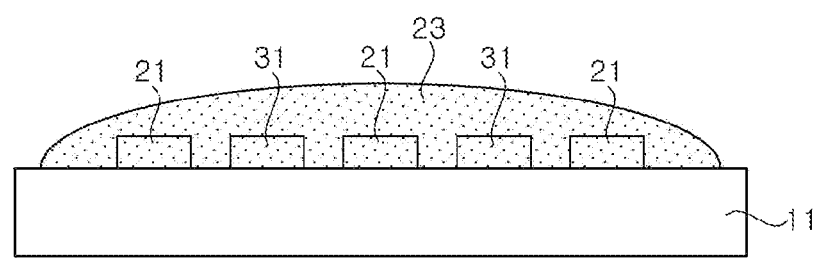
FIG. 7 is a schematic cross-sectional view illustrating a lighting apparatus according to another exemplary embodiment.

FIG. 7 is a schematic cross-sectional view illustrating a lighting apparatus according to another exemplary embodiment.

Referring to FIG. 7, the lighting apparatus according to the illustrated exemplary embodiment is generally similar to the lighting apparatus described with reference to FIG. 3 and FIG. 4, except that the second light emitting diode 31 is also covered with the wavelength converter 23.

More particularly, the wavelength converter 23 covers not only the first light emitting diode 21 but also the second light emitting diode 31. Since the second light emitting diode 31 generally emits light having a longer wavelength than light emitted from the wavelength conversion substance in the wavelength converter 23, for example, a phosphor, light emitted from the second light emitting diode 31 may be emitted to the outside without being wavelength-converted by the wavelength converter 23.

However, a portion of light emitted from the second light emitting diode 31 may be absorbed by the wavelength converter 23 and lost, and thus, more second light emitting diodes 31 than those in the previous exemplary embodiments may be used to implement the irradiance suitable for cell activation. Meanwhile, light generated by the second light emitting diode 31 may also be used to implement white light.

The second light emitting diodes 31 may be uniformly disposed between the first light emitting diodes 21, and thus, uniform light may be emitted to the outside, without being limited thereto.

When the first light emitting diode 21 emits light having the central wavelength in the range of 300 nm to 420 nm, the number and intensity of the second light emitting diodes 31 are adjusted so that the irradiance of light generated by the second light emitting diodes 31 and emitted to the outside without wavelength conversion is greater than that of light generated in the first light emitting diodes 21 and emitted to the outside without wavelength conversion.

Accordingly, the lighting apparatus according to illustrated exemplary embodiment also provides an effective cell activating function by the second light emitting diode 31.

Figure 8:
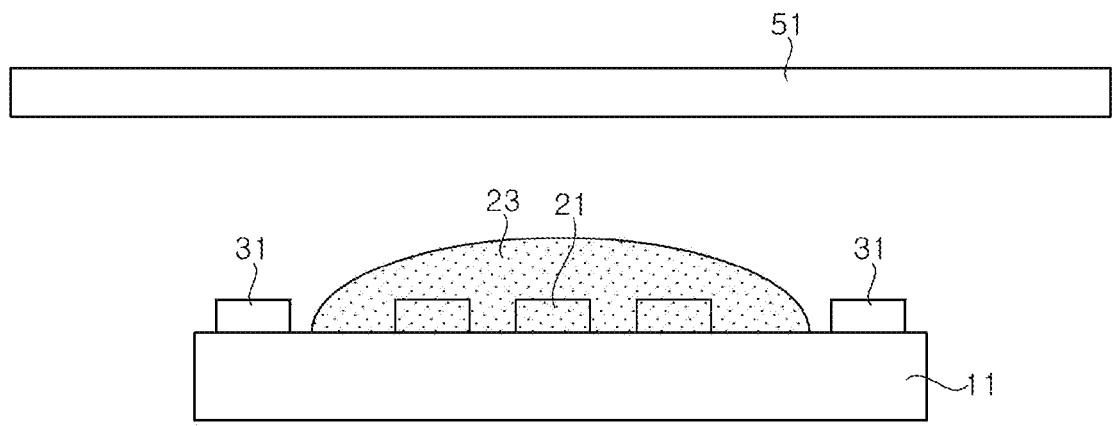
FIG. 8 is a schematic cross-sectional view illustrating a lighting apparatus according to another exemplary embodiment.

FIG. 8 is a schematic cross-sectional view illustrating a lighting apparatus according to another exemplary embodiment.

Referring to FIG. 8, the lighting apparatus according to the illustrated exemplary embodiment is generally similar to the lighting apparatus described with reference to FIG. 3 and FIG. 4, except that it further includes a diffusion plate 51.

The diffusion plate 51 provides uniform light by mixing the white light and light emitted from the second light emitting diode 31. Accordingly, visibility of light emitted from the second light emitting diode 31 may be reduced.

Figure 9:
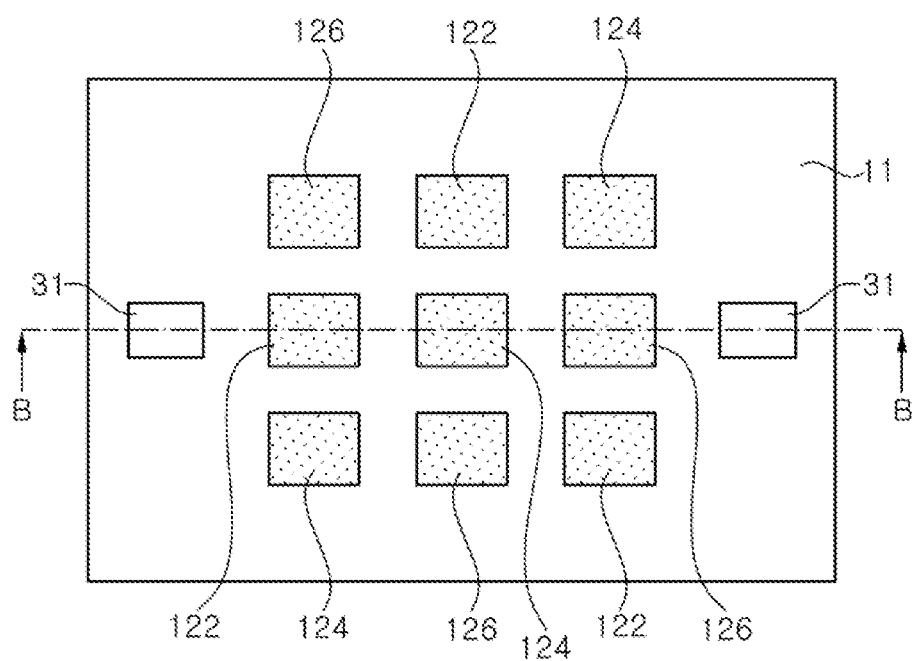
FIG. 9 is a plan view illustrating a lighting apparatus according to another exemplary embodiment.
Figure 10:
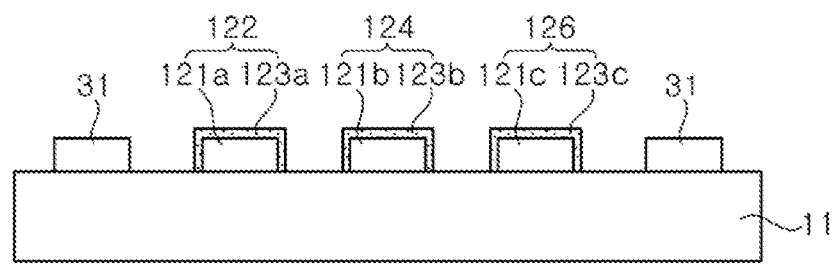
FIG. 10 is a schematic cross-sectional view taken along line B-B of FIG. 9.

FIG. 9 is a schematic plan view illustrating a lighting apparatus according to another exemplary embodiment, and FIG. 10 is a schematic cross-sectional view taken along line B-B of FIG. 9.

Referring to FIG. 9 and FIG. 10, the lighting apparatus according to the illustrated exemplary embodiment includes a substrate 11, a first light emitting unit 122, a second light emitting unit 124, a third light emitting unit 126, and a second light emitting diode 31. Since the substrate 11 and the second light emitting diode 31 are similar to those described with reference to FIG. 3 and FIG. 4, repeated descriptions thereof will be omitted to avoid redundancy.

The first light emitting unit 122 includes a first first-light emitting diode 121a and a first wavelength converter 123a, the second light emitting unit 124 includes a first second-light emitting diode 121b and a second wavelength converter 123b, and the third light emitting unit 126 includes a first third-light emitting diode 121c and a third wavelength converter 123c.

In an exemplary embodiment, the first first- to first third-light emitting diodes 121a, 121b, and 121c may emit light having a central wavelength in a range of about 300 nm to about 420 nm, respectively. In particular, the first first- to first third-light emitting diodes 121a, 121b, and 121c may have a central wavelength in a range of about 400 nm to about 420 nm. These may be the same light emitting diodes within these ranges, or may be light emitting diodes having different central wavelengths.

The first to third wavelength converters 123a, 123b, and 123c include a blue wavelength conversion substance for converting light emitted from the light emitting diode into blue light, respectively. The first to third wavelength converters 123a, 123b, and 123c may also include a green wavelength conversion substance for converting light emitted from the light emitting diode into green light, and a red wavelength conversion substance for converting light emitted from the light emitting diode into red light, respectively. The blue conversion substance, the green wavelength conversion substance, and the red wavelength conversion substance may be selected from the blue phosphor, the green phosphor, and the red phosphor described with reference to FIG. 3 and FIG. 4. In some exemplary embodiments, at least one of these phosphors may also be replaced with quantum dots.

The first to third light emitting units 122, 124, and 126 may emit white light having different color temperatures. As such, the first to third wavelength converters may include different wavelength conversion substances, or different amounts of wavelength conversion substances.

The first to third light emitting units 122, 124, and 126 may be independently driven. For example, the first light emitting unit 122 may implement white light having a color temperature of 6000K or 6500K, the second light emitting unit 124 may implement white light having a color temperature of 2700K, and the third light emitting unit 126 may implement white light having a color temperature of 4000K. As such, the first to third light emitting units are selectively driven for a day, and thus, the color temperature of the lighting apparatus may be changed in accordance with the change of sunlight. In some exemplary embodiments, the first to third light emitting units 122, 124, and 126 may be driven together, and may implement white light having a desired color temperature together.

In irradiance spectrum of light emitted to the outside, an irradiance of the central wavelength of light generated by each of the light emitting diodes 121a, 121b, and 121c in the first to third light emitting units 122, 124, and 126 and emitted to the outside without wavelength conversion is less than that of a peak wavelength of blue light emitted from the corresponding to respective wavelength converters 123a, 123b, and 123c. Accordingly, eye diseases or skin diseases may be prevented by the lighting apparatus.

The second light emitting diode 31 may be driven together when at least one of the first to third light emitting units 122, 124, and 126 is driven. In addition, the second light emitting diode 31 may be driven independently of the first to third light emitting units 122, 124, and 126, and thus, the second light emitting diode 31 may be driven even when the first to third light emitting units 122, 124, and 126 are not driven. Therefore, the second light emitting diode 31 may operate to perform the cell activating function even at night when the lighting apparatus is not used.

The first to third light emitting units 122, 124, and 126 may be disposed so that each of the light emitting units is evenly distributed. In the illustrated exemplary embodiment, although the second light emitting diodes 31 are shown to be disposed outside of locations where the first to third light emitting units 122, 124, and 126 are disposed, the inventive concepts are not limited thereto, and may be disposed together with the first to third light emitting units 122, 124, and 126 in some exemplary embodiments.

FIG. 9 exemplarily illustrates that the number of the first first- to first third-light emitting diodes 121a, 121b, 121c are greater than the number of the second light emitting diodes 31, however, the inventive concepts are not limited thereto.

The first to third light emitting units 122, 124, and 126 have structures where the wavelength converters 123a, 123b, and 123c surround the light emitting diodes 121a, 121b, and 121c. For example, these light emitting units may be chip scale packages. However, the inventive concepts are not limited thereto, and in some exemplary embodiments, the light emitting units 122, 124, and 126 may be light emitting devices having the form of a conventional package well known in the art.

In addition, in the illustrated exemplary embodiment, it is described that the color temperature is changed by using three kinds of light emitting units 122, 124, and 126, but in some exemplary embodiments, four or more kinds of light emitting units, or two kinds of light emitting units may be used to implement various color temperatures. For example, by adjusting intensities of the first light emitting unit 122 and the second light emitting unit 124, light of an intermediate color temperature between the color temperatures of the first light emitting unit and the second light emitting unit may be variously implemented. In this case, the third light emitting unit 126 may be omitted. Alternatively, it is possible to implement light of various color temperatures by including more light emitting units and driving them in turn.

The first first- to first third-light emitting diodes 121a, 121b, and 121c are described as each having the central wavelength in the range of 300 nm to 420 nm, but the inventive concepts are not limited thereto. In some exemplary embodiments, a light emitting unit having a low color temperature, for example, the second light emitting unit 124 may include a blue light emitting diode and a wavelength converter. As such, the first second-light emitting diode 121b may have a central wavelength in a range of 300 nm to 470 nm. The light emitting unit having the low color temperature may be used without causing eye diseases or skin diseases because the intensity of blue light emitted to the outside is weak even when the blue light emitting diode is used as in the conventional light emitting unit. The third light emitting unit 126 representing the intermediate color temperature may also employ the blue light emitting diode if the intensity of blue light emitted to the outside is weak. However, since the first light emitting unit 122 has a high color temperature, a light emitting diode having a central wavelength of about 420 nm or less may be employed.

When the second light emitting unit 124 or the third light emitting unit 126 employs the blue light emitting diode, they may use a green phosphor and a red phosphor, or may use an orange phosphor, rather than using the blue phosphor.

Figure 11:
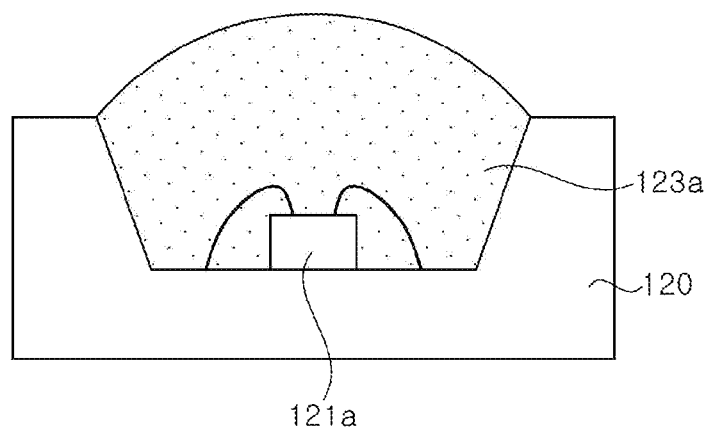
FIG. 11 is a schematic cross-sectional view illustrating a light emitting unit according to another exemplary embodiment.

FIG. 11 is a schematic cross-sectional view illustrating a light emitting unit according to another exemplary embodiment. FIG. 11 schematically shows a light emitting device in the form of a conventional package.

Referring to FIG. 11, the first light emitting unit 122 includes a first first-light emitting diode 121a and a first wavelength converter 123a. The first first-light emitting diode 121a may be mounted in a cavity of a housing 120, and the first wavelength converter 123a covers the light emitting diode 121a in the cavity. The first first-light emitting diode 121a may be electrically connected to lead electrodes through bonding wires.

The package of FIG. 11 is an example, and various kinds of packages may be used. In addition, the first wavelength converter 123a may cover the light emitting diode 121a in various shapes.

Although the light emitting device of FIG. 11 is exemplarily illustrated with reference to the first light emitting unit 122, the second light emitting unit 124 and the third light emitting unit 126 may also be provided in the same package form.

In addition, the second light emitting diode 31 may also be provided as a light emitting device in a package form and mounted on the substrate 11. However, the second light emitting diode 31 may be covered with a transparent molding member rather than being covered with the wavelength converter.

Lighting apparatuses according to exemplary embodiments may change the color temperature of white light in response to the change in the color temperature of sunlight over time. Furthermore, the lighting apparatuses according to exemplary embodiments may change the color temperature of white light in consideration of the change in the color temperature of sunlight according to a region.

Figure 12:
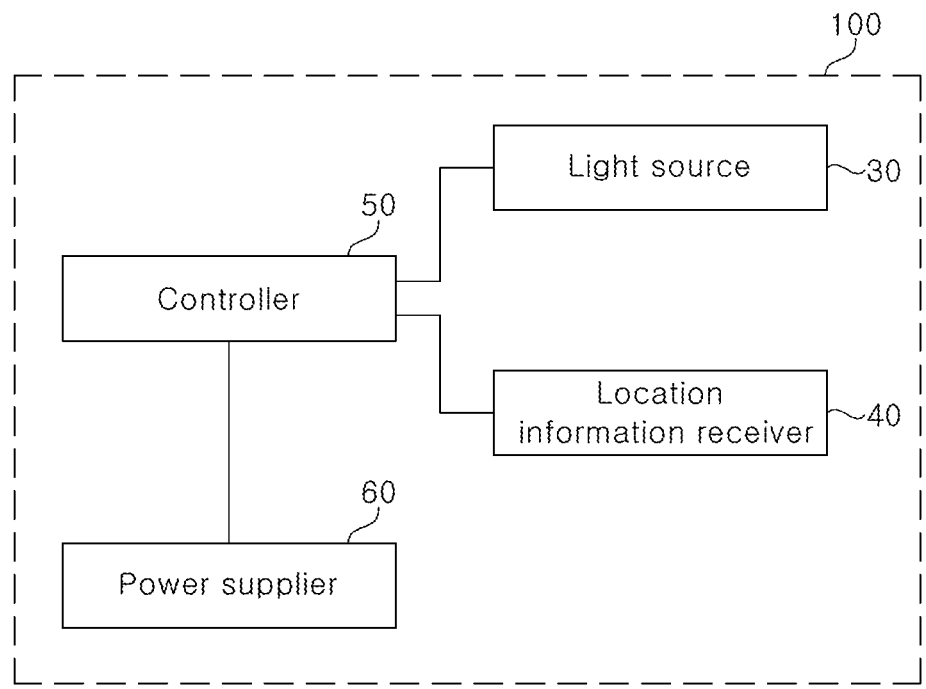
FIG. 12 is a block diagram illustrating a lighting apparatus according to an exemplary embodiment.

FIG. 12 is a block diagram illustrating a lighting apparatus 100 according to an exemplary embodiment.

Referring to FIG. 12, the lighting apparatus 100 according to an exemplary embodiment includes a light source 30 emitting light, a location information receiver 40 for receiving location information, and a controller 50 receiving the location information from the location information receiver and controlling a dose of light emitted from the light source 30. As used herein, the location information may refer to information that can be obtained by using a global positioning system (GPS), and the light source 30 may refer to a white light source that implements white light and capable of changing the color temperature. For example, the light source 30 may be the white light emitting device including the first light emitting diode 21 and the wavelength converter 23, or the first to third light emitting units 122, 124, and 126, without being limited thereto.

The location information receiver 40 receives the location information from a satellite using GPS to calculate current location information of the lighting apparatus 100. The location information may include latitude and longitude, and the location information such as current latitude and longitude of the lighting apparatus 100 may be obtained by location information received by the location information receiver 40. The location information obtained by using the location information signal is provided to the controller 50.

The controller 50 calculates a dose of light to be emitted by the light source 30 based on the location information provided by the location information receiver 40, and controls the light source 30 to emit light as much as the dose of light. In particular, the controller 50 may control whether light is emitted or not, the amount of light, an intensity of light, an emission time, and the like. The controller 50 may also control a dose of light to be emitted from the second light emitting diode 31 to sterilize pathogenic microorganisms together with the dose of the light source 30. In particular, the controller 50 may control the dose of light emitted from the second light emitting diode 31 according to the dose of the white light source 30.

The power supplier 60 is electrically connected to the controller 50 to supply power to the light source 30 and the location information receiver 40. In FIG. 12, the power supplier 60 is illustrated as suppling power to the light source 30 and the location information receiver 40 through the controller 50, but the inventive concepts are not limited thereto. For example, in some exemplary embodiments, the light source 30 and the location information receiver 40 may be directly connected to the power supplier 60, respectively.

The light source 30 and the location information receiver 40 may be disposed on the substrate 11. However, the inventive concepts are limited thereto, and the location information receiver 40 may be disposed on a substrate different from the substrate 11 on which the light source 30 is disposed.

Sunlight is not irradiated at the same intensity to all places on the earth. As the latitude becomes lower, the dose of sunlight becomes larger, and, as the latitude becomes higher, the dose of sunlight becomes smaller. In addition, the altitude becomes higher, the dose of sunlight becomes larger, and, as the altitude becomes lower, the dose of sunlight becomes smaller. Accordingly, depending on which country and in which place a user of the lighting apparatus 100 is present, the time or degree of exposure to sunlight may vary.

In an exemplary embodiment, a location of the lighting apparatus 100 is determined by using location information, and a dose of sunlight is calculated at the location. Then the visible light corresponding to the dose of sunlight is irradiated to a user, and thus the user may obtain the effect of being exposed to sunlight within a harmless limit to the human body, which will be described in more detail below.

Figure 13:
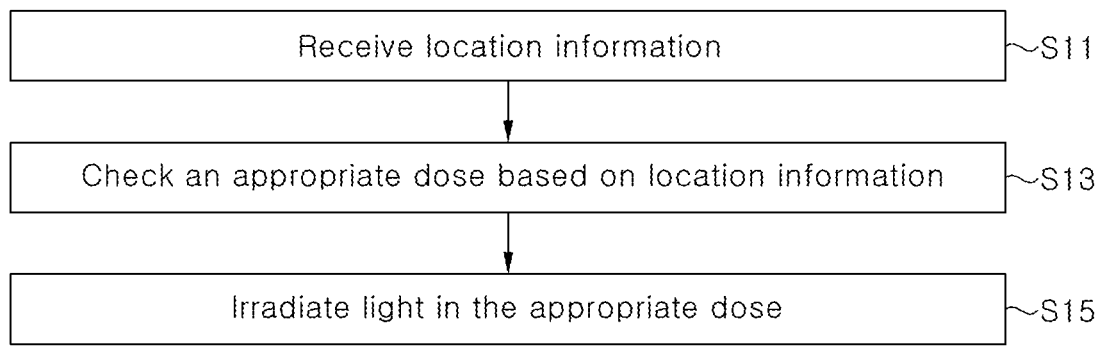
FIG. 13 is a flowchart illustrating a method of driving a light irradiation apparatus according to an exemplary embodiment.

FIG. 13 is a flowchart illustrating a method of driving a light irradiation apparatus according to an exemplary embodiment.

Referring to FIG. 13, a location information receiver receives location information in S11. For example, it may be determined that the light irradiation apparatus is located in city B of country A according to the location information obtained from the location information receiver.

The received location information is provided to a controller, and the controller checks or calculates an appropriate dose of light to be emitted by the light irradiation apparatus based on the location information in S13. For example, when city B of country A is determined, in addition to the latitude and longitude information of city B of country A, information, such as sunrise time, sunset time, and average amount of sunlight may be calculated. When using the latitude and longitude information, the sunrise and sunset time on the latitude and longitude may be easily confirmed, and thus, the controller may be configured to determine whether it is a day or night using an algorithm that calculates the sunrise and sunset time based on the current latitude and longitude.

Using the information such as sunrise time, sunset time, and average amount of sunlight, the controller may calculate the turn-on time, turn-off time, light intensity, etc. of the light source, so as to have a similar dose to that of the actual sunlight, that is, to have an appropriate dose. In particular, the controller may properly adjust whether the light source is to irradiated or not by accurately determining the day or night light without adding an illumination sensor.

The information such as sunrise time, sunset time, and average amount of sunlight at each location may be stored in a separate memory in the controller, or may be easily obtained by accessing a separate internet network or the like.

The controller is configured to irradiate light in a dose corresponding to the appropriate dose calculated by turning on or off the light source, to the user from the light source in S15. The user may be irradiated with the dose substantially the same as that of sunlight at the place where he or she is, even if he or she does not go outdoors.

According to an exemplary embodiment, even if the user is in an environment where he or she is hardly exposed to sunlight, for example, living indoors for a long time, being in a hospital room or a limited space, or mainly being active at night, light similar to sunlight at the present location may be provided in an appropriate dose for a suitable time. Accordingly, the user may be in a familiar environment, psychological stability of the user may be possible, and the irradiation time may also be controlled by setting the sunrise or sunset time, thereby easily recovering the daily biorhythm.

In the exemplary embodiment described above, although it has been described that a single light is used based on the location information, the inventive concepts are not limited thereto. In some exemplary embodiments, the light irradiation apparatus may be used as a correction light source that compensates for a lack of external light in the presence of natural light, i.e., external light emitted from sunlight or lighting apparatuses. For example, in a place with high latitude, the amount of sunlight may be significantly lower than in a region with low latitude, in which case it is necessary to compensate for the lack of sunlight. When the amount of sunlight is low, not only light in the visible light wavelength band irradiated to the user may be insufficient, but also light in the ultraviolet light wavelength band may be insufficient. In this case, the light irradiation apparatus according to an exemplary embodiment may serve to compensate for the insufficient light by additionally irradiating light of the visible light wavelength band and light of the ultraviolet wavelength band.

Figure 14:
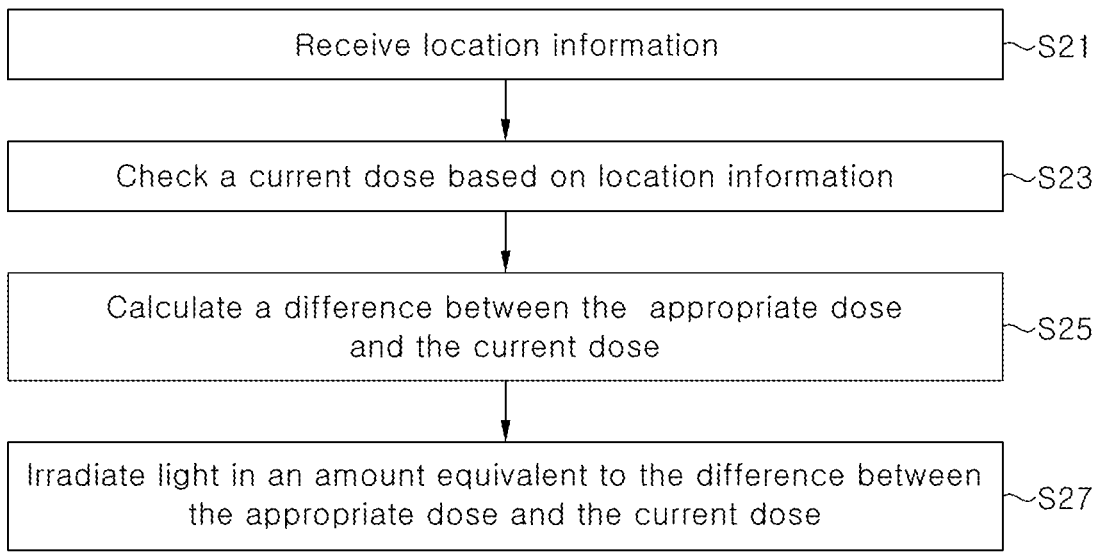
FIG. 14 is a flowchart illustrating a method of driving the light irradiation apparatus according to another exemplary embodiment.

FIG. 14 is a flowchart illustrating a method of driving the light irradiation apparatus according to an exemplary embodiment.

Referring to FIG. 14, a location information receiver receives location information in S21. For example, it may be determined that the light irradiation apparatus is located in city D of country C according to the location information obtained from the location information receiver.

The received location information is provided to a controller, and the controller calculates information such as sunrise time, sunset time, and average amount of sunlight at a current location based on the location information, and, using the information such as sunrise time, sunset time, and average amount of sunlight, calculates a current dose of actual sunlight in S23.

Next, a difference between an appropriate dose required for the user and the current dose is calculated in S25. For example, when city D of country C is located in a region with high latitude and an amount of sunlight is insufficient, the amount of sunlight actually required is the appropriate dose, and a value obtained by subtracting the current dose from the appropriate dose is an insufficient dose. The appropriate dose required for the user may be stored in a separate memory or the like in the controller, or may be easily obtained by connecting to a separate internet network or the like.

The controller is configured to irradiate light in a dose corresponding to the difference between the appropriate dose calculated by turning on or off the light source and the external light dose, that is, light with the insufficient dose, to a target object from the light source in S27.

The user may be irradiated with the predetermined light in the dose most appropriate to the user regardless of the place where he or she is.

Although various lighting apparatuses have been described above, the inventive concepts are not limited thereto. In addition, the lighting apparatus may be installed in not only an indoor living space but also an indoor space used by a plurality of people, such as a hospital or an airport. As such, a lighting system in which the lighting apparatus is installed may also be provided. This lighting system may be suitable for producing the cell activating substance, and may operate the lighting apparatus to effectively produce the cell activating substance even when people are inactive.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A lighting apparatus, comprising:
   a white light emitting device including at least one first light emitting diode and a wavelength converter to implement white light; and
   at least one second light emitting diode configured to emit light that causes a target to produce a cell activating substance upon irradiation,
   wherein:
   the first light emitting diode is configured to emit light having a central wavelength in a range of about 300 nm to about 420 nm;
   the second light emitting diode is configured to emit light having a central wavelength in a range of about 605 nm to about 935 nm;
   the wavelength converter comprises a plurality of wavelength conversion substances to convert light of the first light emitting diode into white light;
   the lighting apparatus is configured to emit the white light implemented in the white light emitting device and light generated by the second light emitting diode to the outside of the lighting apparatus; and
   the white light emitting device is configured to have, in irradiance spectrum of the white light implemented in the white light emitting device, an irradiance at the central wavelength of light emitted from the first light emitting diode to be less than that at a peak wavelength of blue light emitted from the wavelength conversion substance.

2. The lighting apparatus of claim 1, wherein the cell activating substance is nitric oxide (NO) produced by cytochrome c oxidase activity in mitochondria.

3. The lighting apparatus of claim 1, wherein the second light emitting diode is configured to emit light having a central wavelength of about 605 nm to about 655 nm, about 685 nm to about 705 nm, about 790 nm to about 840 nm, or about 875 nm to about 935 nm.

4. The lighting apparatus of claim 1, wherein the wavelength converter comprises a phosphor or a quantum dot.

5. The lighting apparatus of claim 4, wherein light emitted from the second light emitting diode is emitted to the outside of the lighting apparatus without passing through the wavelength converter.

6. The lighting apparatus of claim 1, wherein the first light emitting diode is configured to emit light having a central wavelength in a range of about 400 nm to about 420 nm.

7. The lighting apparatus of claim 1, wherein an irradiance of light generated by the at least one second light emitting diode and emitted to the outside of the lighting apparatus is greater than that of red light wavelength-converted by the wavelength converter and emitted to the outside of the lighting apparatus.

8. The lighting apparatus of claim 7, wherein the lighting apparatus comprises a greater number of first light emitting diodes than that of the at least one second light emitting diode.

9. The lighting apparatus of claim 7, wherein an irradiance of light generated by the at least one second light emitting diode and emitted to the outside of the lighting apparatus is less than or equal to 570 W/m$^2$.

10. The lighting apparatus of claim 1, further comprising a circuit board on which the first light emitting diode and the second light emitting diode are mounted.

11. The lighting apparatus of claim 1, wherein the second light emitting diode is exposed from the wavelength converter and is configured to emit light with a greater irradiance than that from the white light emitting device at a same wavelength.

12. A lighting apparatus, comprising:
a first light emitting unit comprising a first light emitting diode configured to emit light having a central wavelength in a range of about 300 nm to about 420 nm and a first wavelength converter;
a second light emitting unit comprising a second light emitting diode configured to emit light having a central wavelength in a range of about 300 nm to about 470 nm and a second wavelength converter;
at least one secondary light emitting diode configured to emit light having a central wavelength in a range of about 605 nm to about 935 nm,
wherein:
the first light emitting unit is configured to emit light having a higher color temperature than that of the second light emitting unit;
the first wavelength converter comprises a blue wavelength conversion substance for converting light emitted from the first light emitting diode into blue light; and
the lighting apparatus is configured to have, in irradiance spectrum of light emitted to the outside of the lighting apparatus, an irradiance at the central wavelength of light generated by the first and second light emitting diodes and emitted to the outside of the lighting apparatus without wavelength conversion to be less than that at a peak wavelength of wavelength-converted light emitted from the first and second wavelength converters.

13. The lighting apparatus of claim 12, further comprising a third light emitting unit comprising a third light emitting diode configured to emit light having a central wavelength in a range of about 300 nm to about 470 nm and a third wavelength converter,
wherein:
the third light emitting unit is configured to emit light having a higher color temperature than that of the second light emitting unit; and
in irradiance spectrum of light emitted to the outside of the lighting apparatus, an irradiance at the central wavelength of light generated by the third light emitting diode and emitted to the outside of the lighting apparatus without wavelength conversion is less than that at a peak wavelength of wavelength-converted light emitted from the third wavelength converter.

14. The lighting apparatus of claim 13, wherein each of the first, second, and third wavelength converters further includes a green wavelength conversion substance to convert light emitted from the first light emitting diode into green light and a red wavelength conversion substance to convert light emitted from the first light emitting diode into red light.

15. The lighting apparatus of claim 13, wherein the first light emitting unit, the second light emitting unit, and the third light emitting unit are configured to be driven independently from one another.

16. The lighting apparatus of claim 13, wherein the first, second, and third light emitting diodes are configured to emit light having a central wavelength in a range of about 400 nm to about 420 nm.

17. The lighting apparatus of claim 12, wherein:
the second light emitting diode is configured to emit light having a central wavelength of about 605 nm to about 655 nm, about 685 nm to about 705 nm, about 790 nm to about 840 nm, or about 875 nm to about 935 nm; and
the cell activating substance is nitric oxide (NO) produced by cytochrome c oxidase activity in mitochondria.

18. The lighting apparatus of claim 12, wherein:
light wavelength-converted by the wavelength converter and light emitted from the second light emitting diode are configured to be mixed and emitted to the outside of the lighting apparatus; and
the mixed light is white light.

19. The lighting apparatus of claim 18, further comprising a diffusion plate configured to mix light wavelength-converted by the wavelength converter and light emitted from the second light emitting diode.

20. The lighting apparatus of claim 12, wherein a number of the first and second light emitting diodes disposed is greater than a number of the secondary light emitting diode, respectively.

21. The lighting apparatus of claim 12, further comprising a circuit board on which the first and second light emitting diodes and the secondary light emitting diode are mounted.

22. A lighting system comprising a lighting apparatus installed indoors, the lighting apparatus comprising:
a white light emitting device including at least one first light emitting diode and a wavelength converter to implement white light; and
at least one second light emitting diode configured to emit light that causes a target to produce a cell activating substance upon irradiation,
wherein:
the first light emitting diode is configured to emit light having a central wavelength in a range of about 300 nm to about 420 nm;

the second light emitting diode is configured to emit light having a central wavelength in a range of about 605 nm to about 935 nm;

the wavelength converter comprises a plurality of wavelength conversion substances to convert light of the first light emitting diode into white light, the lighting apparatus is configured to emit the white light implemented in the white light emitting device and light generated by the second light emitting diode to the outside of the lighting apparatus; and the white light emitting device is configured to have, in irradiance spectrum of the white light implemented in the white light emitting device, an irradiance at the central wavelength of light emitted from the first light emitting diode is less than that at a peak wavelength of blue light emitted from the wavelength conversion substance.

23. A lighting system comprising a lighting apparatus installed indoors, the lighting apparatus comprising:

a first light emitting unit comprising a first light emitting diode configured to emit light having a central wavelength in a range of about 300 nm to about 420 nm and a first wavelength converter;

a second light emitting unit comprising a second light emitting diode configured to emit light having a central wavelength in a range of about 300 nm to about 470 nm and a second wavelength converter;

at least one secondary light emitting diode configured to emit light having a central wavelength in a range of about 605 nm to about 935 nm, wherein:

the first light emitting unit is configured to emit light having a higher color temperature than that of the second light emitting unit;

the first wavelength converter comprises a blue wavelength conversion substance for converting light emitted from the first light emitting diode into blue light; and the first light emitting unit is configured to have, in irradiance spectrum of light emitted to the outside of the lighting apparatus, an irradiance at the central wavelength of light generated by the first and second light emitting diodes and emitted to the outside of the lighting apparatus without wavelength conversion to be less than that at a peak wavelength of wavelength-converted light emitted from the first and second wavelength converters.

* * * * *